(12) United States Patent
Mallet

(10) Patent No.: US 7,504,076 B2
(45) Date of Patent: Mar. 17, 2009

(54) APPARATUS AND METHODS FOR PERFORMING PARALLEL PROCESSES

(75) Inventor: Claude R. Mallet, Attleboro, MA (US)

(73) Assignee: Waters Investments Limited, New Castle, DE (US)

( * ) Notice: Subject to any disclaimer, the term of this patent is extended or adjusted under 35 U.S.C. 154(b) by 711 days.

(21) Appl. No.: 11/288,589

(22) Filed: Nov. 29, 2005

(65) Prior Publication Data

US 2006/0127284 A1    Jun. 15, 2006

Related U.S. Application Data

(63) Continuation of application No. PCT/US2004/018040, filed on Jun. 4, 2004.

(60) Provisional application No. 60/476,750, filed on Jun. 6, 2003.

(51) Int. Cl.
*B01J 19/00* (2006.01)

(52) U.S. Cl. .................. 422/130; 422/99; 422/100; 436/180

(58) Field of Classification Search ........... 422/99–100, 422/130; 436/180
See application file for complete search history.

(56) References Cited

U.S. PATENT DOCUMENTS 5,164,159 A    11/1992  Hayashi et al.

OTHER PUBLICATIONS

Mallet et al; "Analysis of a bsic drug by on-line solid-phase extraction liquid chromatography . . . "; Rapid Commun. Mass Spectrom. 2002; 16: 805-813.
Mallet et al; "Evaluation of several solid phase extraction liquid chromatography . . . "; Rapid Commun. Mass Spectrom. 2001; 15: 1075-1083.

*Primary Examiner*—Jill Warden
*Assistant Examiner*—Jyoti Nagpaul
(74) *Attorney, Agent, or Firm*—Anthony J. Janiuk

(57) ABSTRACT

Embodiments of the present invention are directed to an apparatus and method for performing parallel processes. One embodiment of the present invention is directed to an apparatus for performing a process having a plurality of steps in which each step is performed in a vessel by flowing a fluid through said vessel. The steps of the process comprise at least a first step and at least one subsequent step. At least one of the subsequent steps is a final step, and each step has a time associated with its performance, a step period. At least one step has a longest step period, and the total number of steps, times the longest step period equals a process period. The apparatus comprises a plurality of vessels. Each of the plurality of vessels is for performing sequentially all the steps of the process in the process period and each of the plurality of vessels is for performing each step of the process in the longest step period.

37 Claims, 2 Drawing Sheets

APPARATUS AND METHODS FOR PERFORMING PARALLEL PROCESSES

This application claims benefit of and is a continuation of International Application No. PCT/us2004/018040, filed 04 Jun. 2004 and designating the United States, which claims benefit of a priority to U.S. Provisional Application No. 60/476,750, filed Jun. 6, 2003. The content of which is expressly incorporated herein by reference in its entirety.

STATEMENT ON FEDERALLY SPONSORED RESEARCH

N/A

1. Field of the Invention

The present application relates to apparatus and methods for performing processes in parallel. Embodiments of the present invention have particular utility in the analysis of samples for drugs or other compositions of interest with detector devices in which it is desirable to have a continuous flow of processed sample through the detector to maximize efficiency.

2. Background of the Invention

Many technical fields are faced with large numbers of samples that need to be processed to form new materials or to determine the content or composition. Quantitative and qualitative analysis to determine the content or composition and the amount thereof has been a daunting task. Often, the nature of the analysis requires the use of expensive detection technology.

As used in this paper, the term "detector" refers to a device that produces a signal in response to the presence or absence of a composition. A typical detector is in the nature of, by way of example, without limitation, mass spectrometers, optical sensors, such ramon detectors, light scattering detectors, fluorescent detectors, chemi-luminescent detectors, light absorbance detectors, light refraction detectors, electro-chemical detectors, viscosity detectors, nuclear magnetic resonance detectors.

These detectors can be expensive to purchase and operate. Therefore, there is a desire to utilize the detector constantly with the shortest interval between sample from which a result is desired.

The term "sample" will be used to denote any material that is received for processing. In clinical settings a sample may comprise a biological fluid or tissue.

The term "analyte" will be used to mean a composition of interest, potentially present in sample.

The term "chromatography" refers to the separation of compounds based on differences in affinity or adsorbance. In chromatography, compounds are held in a solution of a gas, liquid or supercritical fluid. The solution in which the compound is dissolved is known as the "solvent". The dissolved compounds exhibit differences in adsorbance or affinity to a media that is not dissolved. This media is held in place, stationary to the flow of a solution holding the dissolved compounds.

Chromatography is a common research tool and can be used to process samples for analysis by various detection techniques. Chromatography can be used to grossly separate many compounds from a sample, as an extraction technique. Chromatography can also be utilized as a fine separation technique in which subtle changes in molecular structure and function alter the affinity of the compounds to an immobilized media. Closely related compounds, for example drugs and drug metabolytes, can be effectively separated.

Chromatography can be performed in open systems such as well-like devices, for example a ninety-six well extraction plate, or closed systems. Chromatography columns and cartridges are examples of a closed system. The devices typically have a packing of an immobilized media, such as silica or a polymeric particles, to which compounds adsorb. A sample is flowed through the media and compounds adsorb to the media. The initial flowing of sample on to the media is called "loading". Removing the potential compounds of interest is known as "eluting". Elution is often performed by changing the solvent composition. Preparing the media to receive the sample is known as "conditioning". Ensuring the prior sample is removed from a media, to allow a next sample to be loaded on the media is known as "washing".

These steps of loading, conditioning, washing and the like take time. These steps are awkward to perform manually. In the event there is a detector linked to the apparatus performing extractions, the equipment will have significant time in which no meaningful results are generated.

An apparatus and method for performing parallel processes is desired. Particularly in the analytical field, it is desired to perform extraction steps, in a closed system, separation steps in a closed system with detection without manual intervention.

SUMMARY OF THE INVENTION

Embodiments of the present invention are directed to an apparatus and method for performing parallel processes. One embodiment of the present invention is directed to an apparatus for performing a process having a plurality of steps in which each step is performed in a vessel by flowing a fluid through the vessel. The steps of the process comprise at least a first step and at least one subsequent step. At least one of the subsequent steps is a final step, and each step has a time associated with its performance, a step period. At least one step has a longest step period, and the total number of steps, times the longest step period equals a process period. The apparatus comprises a plurality of vessels. Each of the plurality of vessels is for performing sequentially all the steps of the process in the process period and each of the plurality of vessels is for performing each step of the process in the longest step period. Each of the vessels has an inlet for receiving fluid and an outlet for discharging fluid.

The apparatus further comprises valve means in communication with the inlet of each of the plurality of vessels and in communication with the outlet of each of the plurality of vessels. The valve means is capable of being placed in communication with a plurality of fluid sources for placing a fluid corresponding to a step of the process in the inlet of each of the plurality of vessels and to receive fluid from the outlet of each of the vessels to allow each of the vessels to perform sequentially all the steps of a process, and each of the steps in all of the vessels in the longest step period. The valve means has at least one exit conduit for each outlet for receiving discharging fluid. The valve means is responsive to one or more signals from control means to direct a fluid from at least one of the plurality of fluid sources through the vessel and into an exit conduit for each step of the process.

The apparatus further comprises control means in communication with the valve means and having means to determine the longest period. The control means sends one or more signals to the valve means to perform the process in the plurality of vessels simultaneously and sequentially in which no more than one vessel will complete the final step in any step period.

The apparatus is ideally suited to perform an extraction process or an analytical separation process or both in stages. By way of example, one embodiment features a first stage performing an extraction process. The first stage has at least one exit conduit is an analytical conduit in communication with a separation device or a detector. Those skilled in the art will note that the analytical separation phase may also involve a plurality of steps. One embodiment of the present invention features a second stage for performing a analytical separation.

The detector is selected from the group of detectors comprising mass spectrometers, optical sensors, such ramon detectors, light scattering detectors, fluorescent detectors, chemi-luminescent detectors, light absorbance detectors, light refraction detectors, electrochemical detectors, viscosity detectors, nuclear magnetic resonance detectors. Many of these types of detectors are expensive to procure and operate. The present invention allows the discharge of fluids unrelated to the desired signal and the focusing of the detector to receive a desired fluid for analysis.

Preferably, valve means is in fluid communication with at least one fluid source for placing a sample in a vessel. A preferred fluid source for placing a sample in a vessel is an injector. A preferred injector, an autosampler, is sold commercially as an automated assembly for receiving samples and injecting samples into a fluid stream.

Preferably, the apparatus performing an extraction process has closed vessels such as an extraction column or cartridge. A preferred extraction column or cartridge has a polymeric packing media with particles equal or less than 25 microns and a internal diameter of approximately 2.0 to 3.0. Preferably, the apparatus performing an analytical separation has an analytical separation column. A preferred analytical separation columns is determined by the nature of the compounds which need to be separated.

A preferred control means is a computer processing unit programmed by firm or software. The longest period is set either by programming an anticipated time for the completion of all processes or by one or more detectors that determine when a step or all steps have been completed.

Preferably, the apparatus has a start up procedure. In one embodiment, the control means has a start sequence in which at least one first vessel is selected, which first vessel is not all vessels, from the plurality of vessels. The control means directs the valve means to direct fluid into the first vessel to perform the first step during an initial step period not exceeding the longest step period. After the initial step period a subsequent vessel is selected, which subsequent vessel is not all vessels and not a previously selected vessel, from the plurality of vessels. The control means directs the valve means to direct fluid into the subsequent vessel to perform the first step during a subsequent initial step period not exceeding the longest step period. And, the control means directs the valve means to direct fluid in the first vessel to perform a subsequent step not performed in the preceding step period.

Preferably, the apparatus has one or more pumps in communication with valve means. The pumps are placed in communication with one or more fluid sources. The term "fluid sources" is used broadly to suggest fluids from other processes or fluids in bulk containers and the like. The use of solutions in chromatography applications is well known. And, preferably, at least one of the exit conduits is capable of communication with a waste container to facilitate the proper handling of spent fluids.

Typical steps in a chromatographic process are loading, eluting, wash, reconditioning, and gradient elution. Embodiments of present invention allow these steps to be performed in a closed system with little or no manual intervention.

A further embodiment of the present invention features a method. The method performs a process having a plurality of steps in which each step is performed in a vessel by flowing a fluid through the vessel. The steps comprise at least a first step and at least one subsequent step. At least one of the subsequent steps is a final step. Each step has a step period and at least one step has a longest step period. The total number of steps, times the longest step period, equals a process period. The method has the steps of providing an apparatus having a plurality of vessels. Each of the plurality of vessels is for performing sequentially all the steps of the process in the process period and each of the plurality of vessels for performing each step of the process in the longest step period. Each of the vessels has a inlet for receiving fluid and an outlet for discharging fluid.

The apparatus further has valve means in communication with the inlet of each of the plurality of vessels and in communication with the outlet of each of the plurality of vessels. The valve means is capable of being placed in communication with a plurality of fluid sources for placing a fluid corresponding to a step of the process in the inlet of each of the plurality of vessels and to receive fluid from the outlet of each of the vessels. The valve means allows each of the vessels to perform sequentially all the steps of a process and each of the steps in all of the vessels in the longest step period. The valve means has at least one exit conduit for each outlet for receiving discharging fluid. The valve means responsive to one or more signals from control means to direct a fluid from the plurality of fluid sources through the vessel and into an exit conduit for each step of the process.

The apparatus further comprises control means in communication with the valve means and having means to determine the longest period. The control means sends one or more signals to the valve means to perform the process in the plurality of vessels simultaneously and sequentially in which no more than one vessel will complete the final step in any step period.

The method further comprises the step of operating the apparatus comprising the plurality of vessels, valve means and control means to perform the process in the plurality of vessels simultaneously and sequentially in which no more than one vessel will complete the final step in any step period.

The method is preferably an extraction process or an analytical separation process or both. Preferably, the method is performed in stages comprising a first stage in which an extraction process is performed and a second stage in which an analytical separation is performed. In such situations the apparatus has at least one exit conduit of the first stage in communication with valve means of the second stage as a second stage fluid source and at least one exit conduit of the second stage is in communication with a detector. The longest period is the period of time of the step taking the longest time of both the first stage and the second stage.

The steps of the each process are performed in parallel, offset by one or more steps. Each stage is performed concurrently. Thus, embodiments of the present invention maximize the processing of samples through a detector by allowing steps of washing and conditioning to be performed while the detector receives fluid associated with samples. The present invention allows the processing of samples in a closed automated system removing environmental, user and operator errors and variability.

These and other features and advantages will be apparent from the drawings and detailed description that follow.

DETAILED DESCRIPTION OF THE INVENTION

Embodiments of the present invention will be described herein with reference to the Figures which description and figures depict extraction and analytical separation devices and methods. It will be recognized that features of the present invention have applications beyond chemical analysis and the invention should not be so limited. By way of example, without limitation, embodiments of the present invention have utility in diagnostics, industrial process monitoring and synthesis as well as other applications.

Figure 1:
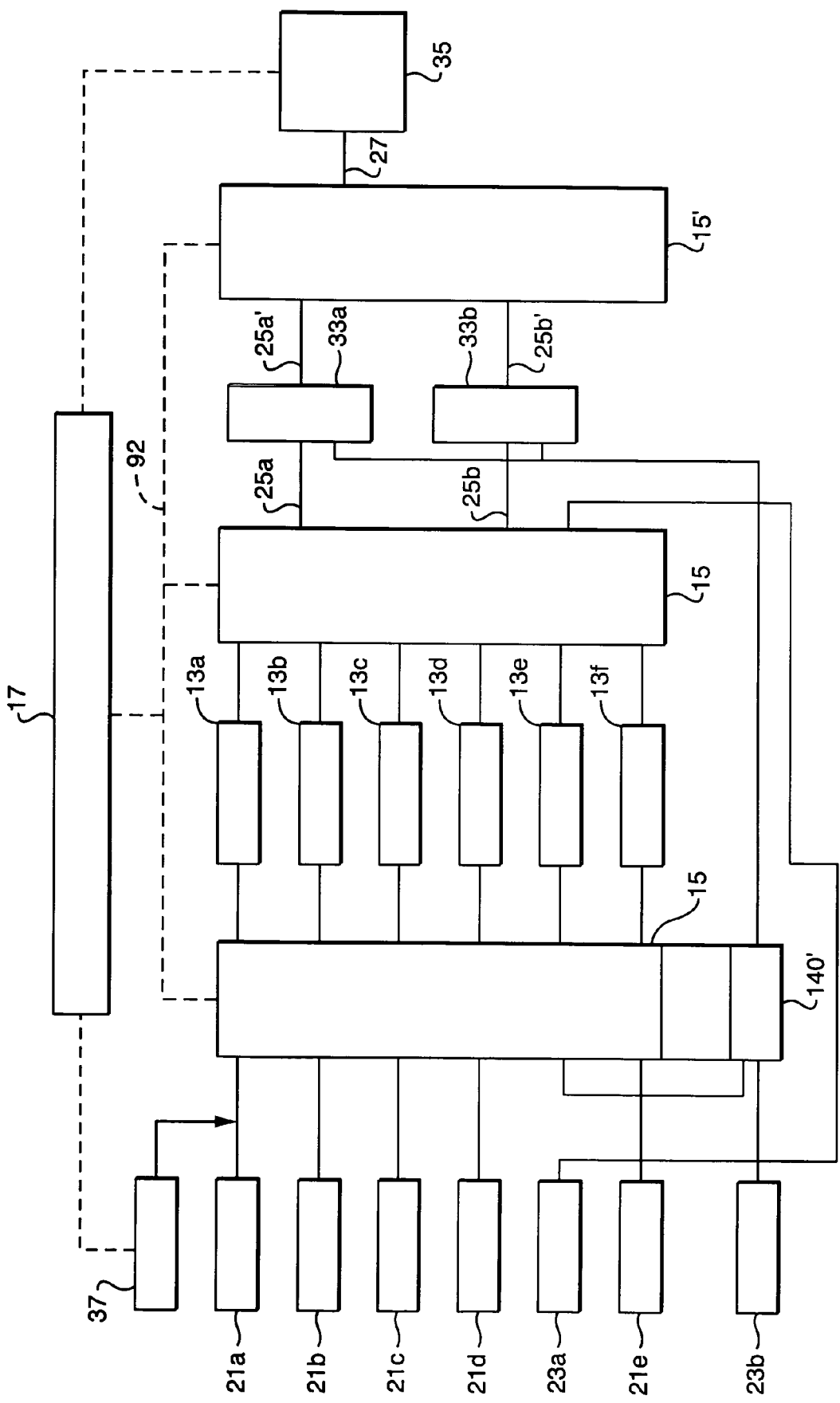
FIG. 1 is a block diagram of an apparatus incorporating features of the present invention; and, FIG. 2 is a block diagram of a process incorporating features of the present invention.

An apparatus embodying features of the present invention, generally designated by the numeral 11, is depicted in block diagram form in FIG. 1. The apparatus 11 has the following major components, a plurality of vessels 13a-f, valve 15, and control means 17. The apparatus 11 is for performing a process having a plurality of steps. Each step is performed in a vessel, such as vessels 13a-f, by flowing a fluid through a vessel. The steps comprising at least a first step and at least one subsequent step, at least one of the subsequent steps is a final step. Each step has a time associated with its completion, a step period. At least one step has a longest step period, and the total number of steps, times the longest step period comprise a process period.

A preferred process is an extraction process. One typical extraction process comprises the steps of loading a sample on a column, washing the column to remove unwanted materials, eluting the desired compound or compounds from the column and reconditioning the column for a next sample. The steps of washing and reconditioning the column can be repeated as desired. For this discussion, the process will have three wash steps, wash 1, wash 2 and wash 3.

Figure 2:
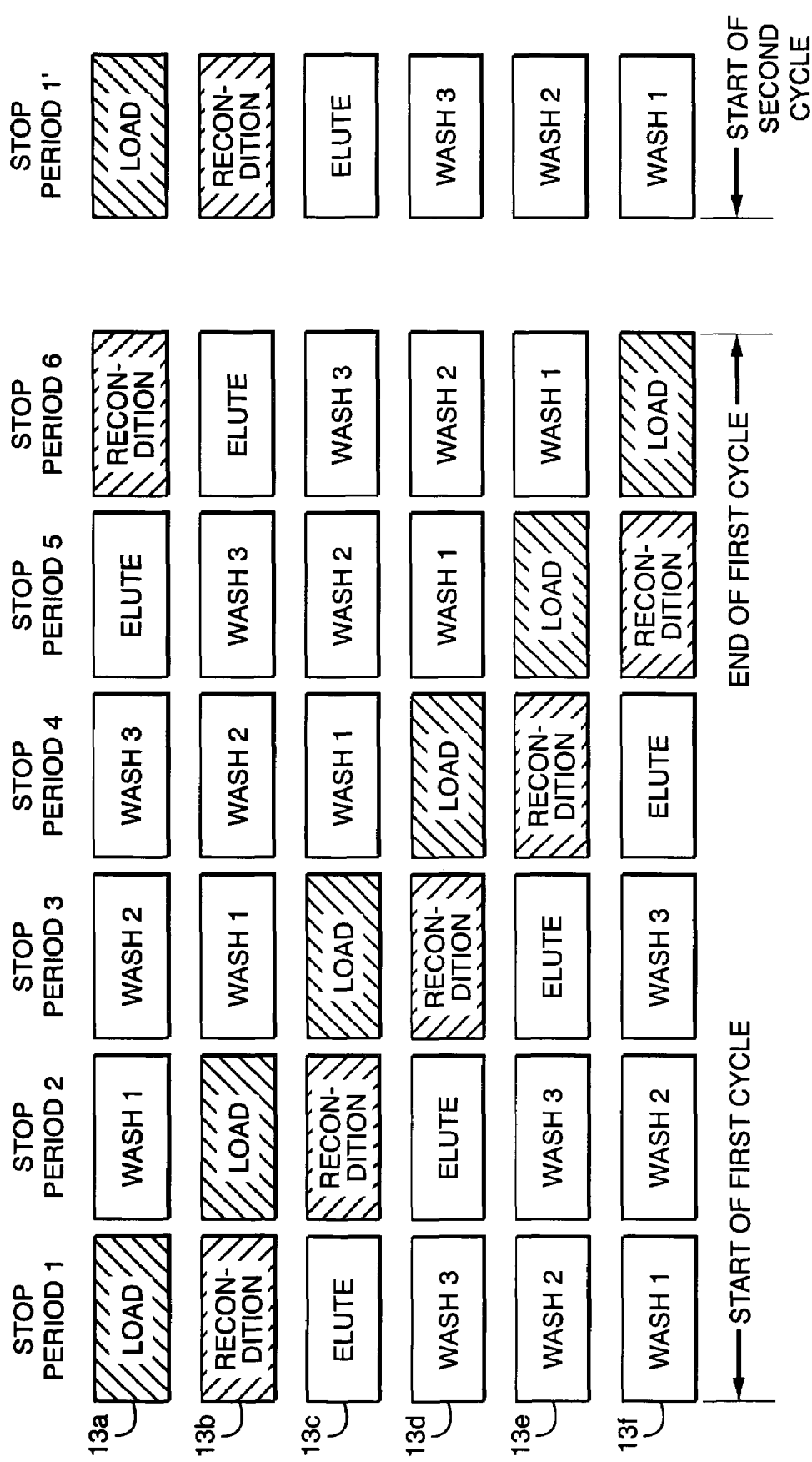

Turning now to FIG. 2, one preferred process, an extraction process, is set forth with respect to the line associated with vessel 13a. The process comprises a load step in Step Period 1, a Wash 1 step in Step Period 2, a Wash 2 step in Step Period 3, a Wash 3 step in Step Period 4, an Elute step in Step Period 5 and a Recondition Step in Step Period 6. In this example, the final step is the Recondition step. Each one of these steps has a time associated with it completion and at least one step has the longest completion time. All steps can be completed within this longest time. The total number of steps, in our example, six, times the time associated with the longest step period equals a process period.

This process resembles an extraction process used with open vessels in a 96 well plate format. The 96 well plate format has identical six steps; a load step in Step Period 1, a Wash 1 step in Step Period 2, a Wash 2 step in Step Period 3, a Wash 3 step in Step Period 4, an Elute step in Step Period 5 and a Recondition Step in Step Period 6.

Returning now to FIG. 1, the apparatus 11 has a plurality of vessels 13a-f. Each of the vessels 13a-f is for performing sequentially all the steps of the process in a process period. Each of the vessels 13a-f is for performing each step of the process in the longest step period. A preferred vessel 13a-f is a chromatographic column or cartridge. Chromatographic columns and cartridges are well known in the art and are not depicted in detail for purposes of simplicity. A typical chromatographic column or cartridge has an inlet for receiving fluid and an outlet for discharging fluid. These columns and cartridges have fittings to be received by conduits.

A particularly advantageous chromatographic cartridge is an OASIS® HLB extraction cartridge packed with 25 micron particles and having dimensions of 2.1 by 20 millimeters. A particularly advantageous chromatographic column is an OASIS® HLB extraction column packed with 20 micron particles and having dimensions of 2.0 by 15 millimeters. These columns and cartridges are capable of performing extraction processes under fast flow conditions with samples that have undergone little or no processing. For example, without limitation, such cartridges and columns are capable of processing blood plasma.

Valve means 15 is in communication with the inlet of each of the vessels 13a-f and in communication with the outlet of each of the vessels 13a-f by way of direct connections or by way of conduits. Conduits are well known in the art and are depicted but not separately identified by number designation for the purpose of simplicity. A typical conduit is flexible stainless steel tubing appropriately sized with respect to fittings on the column or cartridge and the valve means 15.

Valve means 15 is capable of being placed in communication with a plurality of fluid sources represented by pumps 21a-e for placing a fluid corresponding to a step of the process in the inlet of each of the vessels 13a-f. Pumps 21a-f are well known in the art and are commonly plumbed to a bulk container containing one or more solvents and solutions. A preferred pump is a Waters® 515 pump.

Valve means 15 is in communication with the outlet of each of the vessels 13a-f. Thus, the vessels 13a-f receive fluid to perform sequentially all the steps of the process. And, the vessels receive fluid to perform each of the steps in the longest step period. The valve means 15 has at least one exit conduit, of which two are depicted, exit conduit 25a and 25b, for each outlet for receiving discharging fluid. Fluids discharged through exit conduits other than 25a and 25b are directed to waste in an manner known in the art.

The valve means 15 is responsive to one or more signals from control means 17 to direct a fluid from the plurality of fluid sources 21a-e through the vessel 13a-f and into an exit conduit for each step of the process. A preferred valve means 15 are six and ten port valves such as those sold under the trademark LabPRO™ (Rheodyne, Rohnert Park, Calif., USA) and as Waters® Column Selector and Water® Switching Valve (Waters Corporation, Milford, Mass., USA). For the apparatus 11 depicted in FIG. 1 a total of eighteen (18) valves are needed.

Control means 17 is in communication with the valve means 15. That is, control means 17 produces one or more signals which signals are received by valve means 15 to open and close and or change the connection of the vessels 13a-f to the pump 21a-e or a exit conduit 25a and 25b and those not illustrated.

Control means 17 is, preferably, a computer processing unit commonly incorporated in a personal computer. The control means 17 preferably has instrument control software and data management software. A preferred software is Waters® EMPOWER or Water® MASSLINX software (Waters Corporation, Milford, Mass., USA). The control means has means to determine the longest period. The means for determining the longest period can be determined empirically by individuals skilled in the art and programmed into the software program of the control means 17. In the alternative, the apparatus 11 may have a detector [not shown] which monitors an important step for completion.

The control means 17 sends one or more signals to the valve means 15 to perform the process in vessels 15 simultaneously and sequentially in which no more than one vessel will complete the final step in any step period.

By way of example, without limitation, turning now to FIG. 2, vessels 13a-f perform an extraction process. In the six step process, using six vessels 13a-f, only one vessel will complete the process in any step period. Each vessel 13a-f begins the process at a different step period.

Preferably, the apparatus 11 performs an extraction process, as described, or an a analytical separation process or both. As depicted, apparatus 11 performs an extraction process by means of a first stage comprising vessels 13a-f and an analytical separation process in a second stage.

The second stage, the analytical separation process, comprises a load step in Step Period 1, an Elute step in Step Period 2 and a Recondition Step in Step Period 3. In this example, the final step is the Recondition step. Each one of these steps has a time associated with it completion and at least one step has the longest completion time. All steps can be completed within this longest time. The total number of steps, in this example, three, times the time associated with the longest step period equals a process period for the analytical separation process. Preferably, the number of steps in the first stage and the second stage are equal or whole number multiples of each other such that first stage process steps can be matched with second stage process steps with no remainders.

The second stage, the analytical separation process, is performed concurrently with the first stage. A longest step period is determined by comparing the step period having the longest completion time of the first stage with the step period having the longest completion time of the second stage. The steps of the second stage are overlaid over the steps of the first stage such that the second stage process begins with in Step Period 5 of the first stage as depicted in FIG. 2 with the Elute step.

The apparatus 11 has a plurality of vessels 33a and 33b for performing the analytical separation process. Each analytical separation process step is performed in a vessel, such as vessels 33a and 33b, by flowing a fluid through a vessel. The steps comprising at least a first step and at least one subsequent step, at least one of the subsequent steps is a final step. Each step has a time associated with its completion, a step period. At least one step of the first stage and the second stage has a longest step period. The total number of steps of the second stage, times the longest step period comprise a second stage process period. As depicted, the second stage, having fewer steps can be performed twice within the process period for the extraction process stage. If the second stage took the same amount of time, one would most likely desire to increase the number of vessels 33. If the second stage took longer than the first stage, one could have a large number of vessels 33 than vessels 13.

As depicted, separation vessels 33a and 33b are in communication with valve means 15' via conduits 25a' and 25b'. Valve means 15' is in fluid communication with a detector 35 via further a conduit 27. For the purpose of this discussion, detector 35 is a mass spectrometer. However, the detector is a matter of choice. By way of example without limitation, detector 35 can comprise optical sensors, electrochemical sensors, nuclear magnet resonance detectors.

The detection step takes place over a period of time. In the event the detection step is the longest step, the detection step becomes the step in which the all other steps are performed. Embodiments of the present invention allow the use of the detectors for meaningful analysis by controlling and limiting the fluid flowing to the detector to that of desired fluid from the separation vessels of the type represented by separation vessels 25a and 25b.

As illustrated, apparatus 11 has valve means 15 in fluid communication with at least one fluid source 21a for placing a sample in a vessel 13a through 13b. A sample injector 37 is in communication with a conduit [not identified by a numeric designation] linking pump 21a to valve means 15. A preferred sample injector is an autosampler, such as a Model 2777 Autosampler sold by Waters Corporation (Milford, Mass., USA).

Typical autosamplers will receive samples in multi-well devices such 96 well plates. Preferred control means 17 is operated with software capable of monitoring samples from the extraction step, through the separation step and to the detection to record a value associated with such sample 8. A preferred software is Empower® data and instrument management software sold by Waters Corporation (Milford, Mass., USA).

Turning now to FIG. 2, control means 17 has a start sequence in which at least one vessel of vessels 13a through 13f is selected. This first vessel, for discussion purpose this paper will designate 13a, is not all vessels 13a through 13f. Control means 17 directs the valve means 15 to direct fluid into the selected first vessel 13a to perform the first step during an initial step period not exceeding the longest step period.

After the initial step period, a subsequent vessel, which for discussion purpose this paper will designate as vessel 13b, is selected. Again, this subsequent vessel 13b is not all vessels 13a through 13f and not a previously selected vessel 13a. Control means directs the valve means 15 to direct fluid into the subsequent vessel to perform the first step during a subsequent initial step period not exceeding the longest step period. And, control means 15 directs fluid in the first vessel 13a to perform a subsequent step not performed in the preceding step period. This process is repeated until all vessels 13a through 13f are selected. The process is then repeated in an automated manner.

An extraction process is depicted in FIG. 2, performed by vessels 13a through 15. The process has at least one loading step, one elution step, at least one wash step at least one reconditioning step. The wash and reconditioning steps typically product waste fluids.

For purposes of clarity, FIG. 1 does not depict exit conduits in communication with a waste container. Individuals skilled in the art will immediately recognize that the flow of fluid from the extraction devices 13a through 13f and separation devices 33a and 33b which is not directed to the detector 35 are normally directed to a waste container [not shown].

Elution steps can be performed by gradient in which valve means 15 controlled by control means 17 directs fluids from two sources represented by two pumps selected from pumps 21a through 21e to vessels 13a through 13b and or separation vessels 33a and 33b.

The use of the present invention is demonstrated in the following description of a method for performing a process having a plurality of steps. Each step is performed in a vessel by flowing a fluid through the vessel. The steps comprise at least a first step and at least one subsequent step, at least one of the subsequent steps comprising a final step. Each step has a step period in which at least one step has a longest step period, and the total of steps times the longest step period comprise a process period. The method will be described as an extraction, separation and detection process. The extraction steps are performed in a first stage, the separation steps are performed in a second stage and the detection steps are performed in a third stage.

The method comprises the steps of providing an apparatus 11 for performing an analytical process comprising a first extraction phase, a second analytical separation phase, and a third detection stage. The extraction phase, analytical separation phase and detector phase each having a plurality of steps in which each step is performed in a vessel 13a through 13f or 33a and 33b or the detector (normally a closed system in the nature of a vessel) by flowing a fluid through the vessel or detector. The steps comprising at least a first step and at least one subsequent step, at least one of the subsequent steps comprise a final step. Each step has a step period in which at least one step has a longest step period, and the total number of steps, times the longest step period comprise a process period.

The apparatus 11 has a first stage having a plurality of vessels 13a through 13f. Each of the plurality of vessels 13a through 13f perform sequentially all the steps of the extraction process set forth in FIG. 2. The steps of the extraction process are performed in the process period. And, each of the vessels 13a through 13f perform all steps of the process in the longest step period. A typical period is three minutes.

Returning now to FIG. 1, each of the vessels 13a through 13f has an inlet for receiving fluid and an outlet for discharging fluid. The outlet for discharging fluid is plumbed to valve means 15. Valve means directs the fluid from the elution step to the second stage analytical conduits 25a and 25b. The remaining fluid is directed to waste [not shown].

The apparatus 11 has a second stage having a plurality of vessels 33a and 33b. Each of the plurality of vessels 33a and 33b perform sequentially all the steps of the analytical separation process. The steps of the analytical separation process are performed in the process period. And, each of the vessels 33a and 33b perform all steps of the process in the longest step period.

Each of the vessels 33a and 33b has an inlet for receiving fluid and an outlet for discharging fluid. The outlet for discharging fluid is plumbed to valve means 15. Valve means directs the fluid from the separation step to the third stage analytical conduits 33a and 33b and valve means 15' leading to the detector 35. The remaining fluid is directed to waste [not shown].

Valve means 15 and 15" is in communication with the inlet of each of the plurality of vessels 13a-f, or 25a and 25b and the detector 35. Valve means 15 is in communication with the outlet of each of the plurality of vessels 13a through 13f and 25a and 25b. The valve means 15 is capable of being placed in communication with a plurality of fluid sources for placing a fluid corresponding to a step of the process in the inlet of each of the plurality of vessels 13a through 13f and 25a and 25b. And, valve means 15 is capable of receiving fluid from the outlet of each of the vessels 13a through 13f and 25a and 25b to allow each of the vessels to perform sequentially all the steps of an extraction process and separation process respectively. Valve means places such fluids for each of the steps in the vessels in the longest step period. The valve means 15 and 15' is responsive to one or more signals from the control means 17 to direct a fluid from the plurality of fluid sources 21a through 21b and 23a and 23b through the vessels 13a through 13f and 25a and 25b and into an exit conduit for each step of the process.

Control means 17 is in communication with the valve means and having means to determine the longest period. The control means 17 sends one or more signals to the valve means 15 to perform the process in the plurality of vessels 13a through 13f and 25a and 25b and the detector 35 simultaneously and sequentially in which no more than one vessel will complete the final step of a stage in any step period.

A step period typically has a 15 second to five minute duration, although shorter and longer periods are possible. A typical preferred step period is approximately one to three minutes. A start sequence takes place over five periods. With a typical step period of three minutes, the start sequence may take place over a period of fifteen minutes. Embodiments of the present invention exhibit a level of quality of 1.0 picogram to 0.01 nanogram per milliliter. Embodiments of the present invention can process 500 samples per day with a three minute step period, or 1400 samples per day with a one minute step period These and other features and advantages will be apparent to those skilled in the art upon reading the description and reviewing the drawings which disclose preferred embodiments of the invention. Thus, the present invention should not be limited to the precise details set forth herein but should encompass the subject matter of the claims which follow.

The invention claimed is:

1. An apparatus for performing a process having a plurality of steps in which each step is performed in a vessel by flowing a fluid through said vessel, said steps comprising at least a first step and at least one subsequent step, at least one of said subsequent steps comprising a final step, and at least one step in which a product id produced, each step having a step period in which at least one step has a longest step period, said apparatus comprising:

a plurality of vessels, each of said plurality of vessels for performing sequentially all said steps of said process and each of said plurality of vessels for performing each steps of said process in the longest step period, each of said vessels having a inlet for receiving fluid and an outlet for discharging fluid;

valve means in communication with the inlet of each of said plurality of vessels and in communication with the outlet of each of said plurality of vessels, said valve means capable of being placed in communication with a plurality of fluid sources for placing a fluid corresponding to a step of said process in the inlet of each of said plurality of vessels and to receive fluid from the outlet of each of said vessels to allow each of said vessels to perform sequentially all said steps of a process and each of said steps in all of said vessels in said longest step period, and said valve means having at least one exit conduit for receiving discharging a product, said valve means responsive to one or more signals from control means to direct a fluid from said plurality of fluid sources through said vessels for each step of said process and a product into said exit conduit; and;

control means in communication with said valve means and having means to determine the longest period, said control means sending one or more signals to said valve means to perform said process in said plurality of vessels simultaneously and sequentially in which no more than one vessel will complete said final step in any step period.

2. The apparatus of claim 1 wherein said vessels perform an extraction process.

3. The apparatus of claim 2 wherein at least one exit conduit is an analytical conduit, said analytical conduit is capable of being placed in communication with a separation device.

4. The apparatus of claim 2 wherein at least one exit conduit is an analytical conduit said analytical conduit capable of being placed in fluid communication with at least one detector.

5. The apparatus of claim 4 wherein said detector is selected from the group of detectors comprising mass spectrometers, optical sensors, electrochemical sensors, nuclear magnet resonance detectors.

6. The apparatus of claim 4 further comprising a detector.

7. The apparatus of claim 1 wherein said vessels perform an analytical separation process.

8. The apparatus of claim 1 wherein valve means is in fluid communication with at least one fluid source for placing a sample in a vessel.

9. The apparatus of claim 8 wherein said at least one fluid source comprising a sample is an autosampler.

10. The apparatus of claim 1 wherein each of said vessels is an extraction device.

11. The apparatus of claim 1 wherein said control means has a start sequence in which at least one first vessel is selected, which first vessel is not all vessels, from said plurality of vessels, and said control means directs said valve means to direct fluid into said first vessel to perform said first step during an initial step period not exceeding the longest step period.

12. The apparatus of claim 11 wherein after said initial step period a subsequent vessel is selected, which subsequent vessel is not all vessels and not a previously selected vessel, from said plurality of vessels, and said control means directs said valve means to direct fluid into said subsequent vessel to perform said first step during a subsequent initial step period not exceeding the longest step period and to direct fluid in said first vessel to perform a subsequent step not performed in the preceding step period.

13. The apparatus of claim 1 further comprising one or more pumps in communication with one or more fluid sources to place fluid in said valve means.

14. The apparatus of claim 1 wherein at least one of said exit conduits is capable of communication with a waste container.

15. The apparatus of claim 1 wherein said process has at least one loading step and one elution step.

16. The apparatus of claim 15 wherein said process further comprises at least one wash step.

17. The apparatus of claim 15 wherein said process further comprises at least one reconditioning step.

18. A method for performing a process having a plurality of steps in which each step is performed in a vessel by flowing a fluid through said vessel, said steps comprising at least a first step and at least one subsequent step, at least one of said subsequent steps comprising a final step and at least one step in which a product is formed, each step having a step period in which at least one step has a longest step period, said method comprising the steps of providing:

a plurality of vessels, each of said plurality of vessels for performing sequentially all said steps of said process and each of said plurality of vessels for performing each step of said process in the longest step period, each of said vessels having a inlet for receiving fluid and an outlet for discharging fluid;

valve means in communication with the inlet of each of said plurality of vessels and in communication with the outlet of each of said plurality of vessels, said valve means capable of being placed in communication with a plurality of fluid sources for placing a fluid corresponding to a step of said process in the inlet of each of said plurality of vessels and to receive fluid from the outlet of each of said vessels to allow each of said vessels to perform sequentially all said steps of a process and each of said steps in all of said vessels in said longest step period, and said valve means having at least one exit conduit for discharging said product, said valve means responsive to one or more signals from control means to direct a fluid from said plurality of fluid sources through said vessel for each step of said process and said product into an exit conduit; and;

control means in communication with said valve means and having means to determine the longest period, said control means sending one or more signals to said valve means to perform said process in said plurality of vessels simultaneously and sequentially in which no more than one vessel will complete said final step in any step period; and, operating said plurality of vessels, valve means and control means to perform said process in said plurality of vessels simultaneously and sequentially in which no more than one vessel will complete said final step in any step period.

19. The method of claim 18 wherein said vessels perform an extraction process.

20. The method of claim 19 wherein at least one exit conduit is an analytical conduit, said analytical conduit capable of being placed in communication with a separation device.

21. The method of claim 20 wherein said detector is selected from the group of detectors comprising mass spectrometers, optical sensors, electrochemical sensors, nuclear magnet resonance detectors.

22. The method of claim 19 wherein at least one exit conduit is an analytical conduit said analytical conduit is capable of being placed in fluid communication with at least one detector.

23. The method of claim 22 wherein a detector is in communication with said analytical conduit.

24. The method of claim 18 wherein said vessels perform an analytical separation process.

25. The method of claim 18 wherein valve means is in fluid communication with at least one fluid source for placing a sample in a vessel.

26. The method of claim 25 wherein said at least one fluid source comprising a sample is an autosampler.

27. The method of claim 18 wherein each of said vessels is an extraction device.

28. The method of claim 18 wherein said control means has a start sequence in which at least one first vessel is selected, which first vessel is not all vessels, from said plurality of vessels, and said control means directs said valve means to direct fluid into said first vessel to perform said first step during an initial step period not exceeding the longest step period.

29. The method of claim 28 wherein after said initial step period a subsequent vessel is selected, which subsequent vessel is not all vessels and not a previously selected vessel, from said plurality of vessels, and said control means directs said valve means to direct fluid into said subsequent vessel to perform said first step during a subsequent initial step period not exceeding the longest step period and to direct fluid in said first vessel to perform a subsequent step not performed in the preceding step period.

30. The method of claim 18 wherein one or more pumps are in communication with one or more fluid sources to place fluid in said valve means.

31. The method of claim 18 wherein at least one of said exit conduits is capable of communication with a waste container.

32. The method of claim 18 wherein said process has at least loading one step and one elution step.

33. The method of claim 32 wherein said process further comprises at least one wash step.

34. The method of claim 32 wherein said process further comprises at least one reconditioning step.

35. An apparatus for performing a first process in a first stage and a second process in a second stage in which said first stage and second stage each has a plurality of steps in which each step is performed in a vessel by flowing a fluid through said vessel, said steps comprising at least a first step and at least one subsequent step, at least one of said subsequent steps comprising a final step and at least one of said steps producing a product, each step having a step period in which at least one step has a longest step period, said apparatus comprising:

a plurality of first stage vessels, each of said plurality of first stage vessels for performing sequentially all said steps of said first stage process to produce a first stage product and each of said plurality of first stage vessels for performing all steps of said first process in the longest step period, each of said first stage vessels having a inlet for receiving fluid and an outlet for discharging fluid;

a plurality of second stage vessels, each of said plurality of second stage vessels for performing sequentially all said steps of said second stage process to produce a second stage product and each of said plurality of second stage vessels for performing all steps of said second process in the longest step period, each of said second stage vessels having a inlet for receiving fluid and an outlet for discharging fluid;

first stage valve means in communication with the inlet of each of said plurality of first stage vessels and in communication with the outlet of each of said plurality of first stage vessels, said valve means capable of being placed in communication with a plurality of fluid sources for placing a fluid corresponding to a step of said first process in the inlet of each of said plurality of first stage vessels and the inlet of said plurality of second stage vessels and to receive fluid from the outlet of each of said first stage vessels to allow each of said first stage vessels to perform sequentially all said steps of a first stage process and each of said steps in all of said first stage vessels in said longest step period, and said valve means having a plurality of first stage exit conduits for discharging first stage product, said valve means responsive to one or more signals from control means to direct a fluid from said plurality of fluid sources through said vessel for each step of said process and a first stage product into said plurality of exit conduits, each of said first stage exit conduits in communication with at least one of said second stage vessels to place fluid corresponding to a step of the second process in the inlet if each of said second stage vessels to produce a second stage product; and, control means in communication with said valve means and having means to determine the longest period, said control means sending one or more signals to said valve means to perform said first stage process in said plurality of first stage vessels simultaneously and sequentially in which no more than one vessel will complete said final step in any step period to produce a first product and to perform said second stage process simultaneously and sequentially in said second stage vessels as the first stage process is performed to produce a second stage product.

36. The apparatus of claim 35 wherein said valve means is in communication with said outlet of said second stage vessels to receive said second stage product and said valve means has a second stage exit conduit.

37. The apparatus of claim 36 wherein said apparatus has at least one detector in communication with said exit stage conduit.

* * * * *